United States Patent [19]

Sanns, Jr.

[11] 4,344,892

[45] Aug. 17, 1982

[54] SELF-GRANULATING REACTION PRODUCT OF 4,4'-DIPHENYLMETHANE DIISOCYANATE AND RESORCINOL

[75] Inventor: Frank Sanns, Jr., Upper St. Clair, Pa.

[73] Assignee: Mobay Chemical Corporation, Pittsburgh, Pa.

[21] Appl. No.: 292,967

[22] Filed: Aug. 14, 1981

[51] Int. Cl.$^3$ .......................................... C07C 119/048
[52] U.S. Cl. ....................... 260/453 AM; 260/453 SP
[58] Field of Search .................. 260/453 AM, 453 SP

[56] References Cited

U.S. PATENT DOCUMENTS 3,035,078  5/1962  DeLong et al. ............... 260/453 SP
3,644,457  2/1972  König et al. .................. 260/453 SP Primary Examiner—Dolph H. Torrence
Attorney, Agent, or Firm—Gene Harsh; Joseph C. Gil

[57] ABSTRACT

The present invention relates to a free-flowing, dry, granular powder comprising the reaction product of 4,4'-diphenylmethane diisocyanate and resorcinol, the product having an isocyanate group content of from 27 to 31% by weight, and to the process for manufacture thereof.

8 Claims, No Drawings

SELF-GRANULATING REACTION PRODUCT OF 4,4'-DIPHENYLMETHANE DIISOCYANATE AND RESORCINOL

BACKGROUND OF THE INVENTION

The present invention relates to a self-granulating reaction product of 4,4'-diphenylmethane diisocyanate and resorcinol, and to the method of preparation thereof.

It is known that 4,4'-diphenylmethane diisocyanate is solid at room temperature. When such diisocyanate is stored in drums, a solid product is formed which requires heating prior to removal from the drums.

Since 4,4'-diphenylmethane diisocyanate is highly useful in the production of thermoplastic polyurethanes, cast polyurethane elastomers, and many other urethane applications, it would be highly desirable to be able to use 4,4'-diphenylmethane diisocyanate directly from the storage drums without a need to heat such drums. The present invention substantially solves the problem noted above.

DESCRIPTION OF THE INVENTION

The present invention is directed to a reaction product of 4,4'-diphenylmethane diisocyanate and resorcinol and to the method of its manufacture. The resultant product, which generally contains from 27 to 31% by weight of isocyanate groups, is a dry, granular powder which flows freely without any need for heating.

The present process broadly comprises (i) reacting 4,4'-diphenylmethane diisocyanate with resorcinol at a temperature of from 40° to 80° C. in the presence of a catalytic amount of a material which catalyzes the reaction between isocyanate groups and hydroxyl groups, (ii) allowing the reaction mixture to exotherm to a temperature no higher than 90° C., and (iii) allowing the resultant product to cool to room temperature, thereby forming a free-flowing, dry, granular powder.

The product of the present invention is generally produced by mixing the two components and heating them to a temperature of from 40° to 80° C. The catalyst can either be added to the reaction mixture or vice versa. Similarly, the catalyst can be added before or after the heating step. A slight exotherm is generally observed. It is critical to the present invention that the heating temperature be kept at or below 80° C. in order to allow for production of the free-flowing, dry, granular powder. During the exotherm the reaction mixture is maintained at a temperature not exceeding 90° C. As the exotherm subsides, the material upon cooling generally becomes a fluid slush which, if desired, can then be poured on a suitable surface, e.g., an open pan or a slowly moving conveyor belt. Upon standing for from 15 minutes to 2 hours at room temperature, the product becomes a free-flowing dry, granular powder.

In addition to the critical temperature noted above, the amount of resorcinol used also appears to be critical. In general, the amount used should be such that the isocyanate group content of the resultant product is from 27% to 31% by weight. The isocyanate group content of the product is preferably from 28% to 30% by weight. In general, the isocyanate group content noted will be achieved by using from 2 to 7 and preferably from about 2.4 to 5 parts by weight of resorcinol per 100 parts by weight of isocyanate. The melting point of the product is dependent upon the amount of resorcinol used. For example, when using 2.4 parts of resorcinol, the melting point of the product is about 60° C., while use of 5 parts produces a product having a melting point of 90° C.

Suitable catalysts must also be used, which catalysts are generally known in the art for the catalysis of the reaction of isocyanate groups with hydroxyl groups. It is presently preferred to utilize dibutyltin dilaurate and/or triethylene diamine. The catalysts should be used in catalytic amounts and are generally used in amounts of from 0.001 to 5% by weight based on the amount of isocyanate used.

The invention is further illustrated, but is not intended to be limited by the following Examples in which all parts and percentages are by weight unless otherwise specified.

EXAMPLES

EXAMPLE 1

100 parts of 4,4'-diphenylmethane diisocyanate and 2.4 parts of resorcinol were added to a reaction vessel and heated to about 80° C. with slow stirring. One drop of triethylene diamine and one drop of dibutyltin dilaurate were added. The solution exothermed slightly and turned hazy. The solution was held at about 90° C. for five minutes and poured into a 6"×7" aluminum pan. After about 90 minutes, the product had slowly formed a free-flowing, light powder having an isocyanate group content of about 31% by weight.

EXAMPLE 2

100 parts of 4,4'-diphenylmethane diisocyanate and 3 parts of resorcinol were added to a reaction vessel and heated to 55° to 60° C. One drop of dibutyltin dilaurate was added and a slight exotherm was observed. The mixture was cooled to about 55° C. and poured into a 6"×8" aluminum pan. A free-flowing, dry powder resulted.

When the experiment was repeated using catecol, hydroquinone, 4,4'-sulphonyl diphenol, 4,4'-dihydroxydiphenylsulfide, bisphenol A, phenol and 1,6-hexanediol, instead of resorcinol, a powder did not result.

What is claimed is:

1. A free-flowing, dry, granular powder comprising the reaction product of 4,4'-diphenylmethane diisocyanate and resorcinol, the product having an isocyanate group content of from 27 to 31% by weight.

2. The powder of claim 1 having an isocyanate group content of from 28 to 30% by weight.

3. The powder of claim 1, wherein from 2 to 7 parts by weight of resorcinol are reacted per 100 parts by weight of said diisocyanate.

4. The powder of claim 3, wherein from 2.4 to 5 parts by weight of resorcinol are reacted per 100 parts by weight of said diisocyanate.

5. The powder of claim 1, wherein from 0.001 to 5% by weight of a catalyst for the reaction of isocyanate groups and hydroxyl groups is used during formation of the reaction product.

6. A process for the preparation of a free-flowing, dry, granular powder comprising:

(i) reacting 4,4'-diphenylmethane diisocyanate with resorcinol at a temperature of from 40° to 80° C. in the presence of a catalytic amount of a material which catalyzes the reaction between isocyanate groups and hydroxyl groups, (ii) allowing the reaction mixture to exotherm to a temperature no higher than 90° C., and
(iii) allowing the resultant product to cool to room temperature.

7. The process of claim 6, wherein the resultant product has an isocyanate group content of from 27 to 31% by weight.

8. The process of claim 7, wherein said material is used in an amount of from 0.001 to 5% by weight based on the amount of isocyanate.

* * * * *